(12) United States Patent
Delsman

(10) Patent No.: US 8,419,762 B2
(45) Date of Patent: Apr. 16, 2013

(54) SPLIT SHEATH FOR TROCAR ASSEMBLY

(75) Inventor: Jill Delsman, Irvine, CA (US)

(73) Assignee: Senorx, Inc., Tempe, AZ (US)

( * ) Notice: Subject to any disclaimer, the term of this patent is extended or adjusted under 35 U.S.C. 154(b) by 81 days.

(21) Appl. No.: 11/981,007

(22) Filed: Oct. 31, 2007

(65) Prior Publication Data

US 2009/0043328 A1 Feb. 12, 2009

Related U.S. Application Data

(60) Provisional application No. 60/964,079, filed on Aug. 9, 2007.

(51) Int. Cl.
*A61B 17/34* (2006.01)

(52) U.S. Cl.
USPC .......... 606/185; 600/184; 604/164.1

(58) Field of Classification Search .......... 606/184, 606/185, 108, 190; 604/160, 164.1
See application file for complete search history.

(56) References Cited

U.S. PATENT DOCUMENTS

| | | | |
|---|---|---|---|
| 3,844,272 A | 10/1974 | Banko | |
| 4,596,559 A * | 6/1986 | Fleischhacker | 604/164.05 |
| 4,763,642 A | 8/1988 | Horowitz | |
| 4,921,479 A | 5/1990 | Grayzel | |
| 5,104,388 A | 4/1992 | Quackenbush | |
| 5,250,033 A * | 10/1993 | Evans et al. | 604/160 |
| 5,368,591 A | 11/1994 | Lennox et al. | |
| 5,431,676 A * | 7/1995 | Dubrul et al. | 606/185 |
| 5,454,790 A * | 10/1995 | Dubrul | 604/104 |
| 5,620,479 A | 4/1997 | Diederich | |
| 5,647,860 A | 7/1997 | Roth et al. | |
| 5,863,284 A | 1/1999 | Klein | |
| 5,938,582 A | 8/1999 | Ciamacco, Jr. et al. | |
| 6,080,141 A | 6/2000 | Castro et al. | |
| 6,099,499 A | 8/2000 | Ciamacco, Jr. | |
| 6,251,119 B1 | 6/2001 | Addis | |
| 6,306,053 B1 * | 10/2001 | Liechty, II | 473/583 |

(Continued)

FOREIGN PATENT DOCUMENTS

| | | |
|---|---|---|
| EP | 0 093 101 | 11/1983 |
| EP | 0 577 400 | 10/1999 |

(Continued)

OTHER PUBLICATIONS

International Search Report for PCT/US2008/009424 mailed Mar. 11, 2009.

(Continued)

*Primary Examiner* — S. Thomas Hughes
*Assistant Examiner* — Julie A Szpira

(57) ABSTRACT

A trocar assembly including a trocar and a trocar sheath and methods for accessing an intracorporeal site, e.g. biopsy or trocar site, using the trocar assembly. The trocar has a tissue penetrating distal tip, an elongated shaft and a proximal handle portion. The distal portion of the trocar sheath forms a releasable connection, such as a friction fit, with the shaft of the trocar and a slit that extends from the distal portion to the proximal end of the trocar sheath. The trocar assembly is advanced through the patient's tissue until the distal end of the trocar sheath is located at the desired site and then the trocar is removed. A treatment device such as a radiation balloon catheter is advanced through the interior of the sheath until the treatment component thereof is at the desired site.

27 Claims, 10 Drawing Sheets

U.S. PATENT DOCUMENTS

| | | | |
|---|---|---|---|
| 6,458,069 B1 | 10/2002 | Tam et al. | |
| 6,544,277 B1* | 4/2003 | O'Heeron et al. | 606/185 |
| 6,676,590 B1 | 1/2004 | Urick et al. | |
| 6,740,277 B2* | 5/2004 | Howell et al. | 264/209.3 |
| 6,749,554 B1 | 6/2004 | Snow et al. | |
| 7,056,274 B2 | 6/2006 | Apple et al. | |
| 7,294,136 B2* | 11/2007 | Dubrul et al. | 606/185 |
| 7,780,692 B2* | 8/2010 | Nance et al. | 606/198 |
| 2003/0216771 A1 | 11/2003 | Osypka et al. | |
| 2004/0111061 A1 | 6/2004 | Curran | |
| 2005/0124937 A1* | 6/2005 | Kick et al. | 604/164.1 |
| 2008/0021463 A1 | 1/2008 | Georgy | |
| 2009/0292301 A1 | 11/2009 | Hasselman | |

FOREIGN PATENT DOCUMENTS

| | | |
|---|---|---|
| WO | WO 82/03558 | 10/1982 |
| WO | WO 92/08513 | 5/1992 |
| WO | WO 99/17665 | 4/1999 |
| WO | WO 01/34238 | 5/2001 |
| WO | WO 02/36179 | 5/2002 |
| WO | WO 2006/007090 | 1/2006 |

OTHER PUBLICATIONS

Written Opinion for PCT/US2008/009424 mailed Mar. 11, 2009.
International Search Report for PCT/US2008/009424 mailed Dec. 4, 2008.

* cited by examiner

SPLIT SHEATH FOR TROCAR ASSEMBLY

RELATED APPLICATIONS

This application is related to provisional application Ser. No. 60/964,079, filed Aug. 9, 2007, which is incorporated by reference in its entirety and from which priority is claimed.

FIELD OF THE INVENTION

This invention relates generally to the fields of medical treatment devices and methods. In particular, the invention relates to devices and methods for accessing a body cavity for treatment, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

A radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Other inflatable treatment delivery devices and systems may be used to treat cancer in tissue adjacent a body cavity.

However, such radiation, chemotherapy, thermal treatment, and other cancer treatments with balloon catheters are often delivered several days to several weeks after tissue has been removed from the site. Accessing the site from which tissue has been removed in order to place a balloon catheter for treatment can be inconvenient for the surgeon and can require a large accessing pathway.

SUMMARY OF THE INVENTION

This invention is generally directed to treating a patient's body cavity, natural or formed by tissue removal or other intracorporeal site (hereinafter collectively referred to as a body cavity) and devices and methods for such treatments. The invention is particularly suitable for accessing a body cavity formed by the removal of tissue such as in a biopsy or lumpectomy.

More specifically, a trocar assembly embodying features of the invention has a trocar with a tissue penetrating distal tip, and a split sheath introducer or trocar sheath with a short cylindrical distal portion that is configured to provide a releasable connection with the trocar shaft proximal to the tissue penetrating distal tip, Preferably, the slit in the trocar sheath widens in the proximal direction to allow the sheath to guide treatment devices, such as a radiation balloon catheter, to the intracorporeal site. The proximal end of the trocar sheath may be formed to be easily grasped by the surgeon or other personnel, In one embodiment, the cylindrical distal portion of the sheath has a weakened or scored portion in alignment with the slit so that when the trocar is removed, a treatment device having a transverse dimension or expandable to a transverse dimension slightly larger than the internal transverse dimension of the short cylindrical sheath portion can be advanced through the cylindrical portion and break or tear the weakened or scored portion forming a slit along the entire length of the sheath. This facilitates the removal of the trocar sheath from the treatment device without removal of the treatment device.

To access the desired intracorporeal site, the trocar assembly is advanced percutaneously with the aid of the tissue penetrating distal tip until the distal end of the trocar sheath is located at the desired location within the patient's body (such as a prior biopsy site or lumpectomy site). The cylindrical distal portion of the sheath forms a tight friction fit with the shaft of the trocar proximal to the distal tip so that the trocar and the trocar sheath can be advanced as a unitary assembly. Once in position, the trocar is pulled out of the sheath leaving the distal end of the sheath at the desired location. The tissue penetrating distal tip of the trocar has very small transverse dimensions so the pathway form by the trocar tip has much smaller transverse dimensions than conventional procedures. Moreover, if desired a vacuum line can be advanced into the biopsy site to remove fluid therefrom before the treatment device is deployed. A treatment device, such as a radiation balloon catheter with enlarged transverse dimensions in the distal portion, is advanced through the interior of the trocar sheath until the portion of the catheter with enlarged transverse dimensions passes through and breaks the score line on the distal cylindrical end of the sheath. The sheath may then be withdrawn and, because of the broken score line, can be removed from the shaft of the radiation balloon catheter. At that point the radiation treatment may proceed in a conventional manner wherein a radiation source may be advanced through the catheter to a treatment location within the balloon. The balloon may be inflated before the sheath is withdrawn to secure the distal portion of the catheter at the intracorporeal site for treatment. At the end of the treatment, the radiation source and balloon catheter may be withdrawn from the patient and the opening in the patient's skin may be suitably closed by suturing.

The present invention provides a convenient, easy to use trocar assembly for reaccessing biopsy and lumpectomy sites and the like for subsequent treatments. The trocar sheath keeps the passageway open for easy placement of a treatment device. Moreover, the splitting of the sheath during placement of a treatment device makes removal of the sheath a one handed operation. These and other advantages of the present invention are described in more detail in the following written description and the accompanying exemplary drawings.

DETAILED DESCRIPTION OF THE INVENTION

The present invention is directed to a trocar sheath and particularly a trocar assembly with the trocar sheath that provides access to an intracorporeal site for treatment. The trocar assembly is particularly suitable to access a biopsy cavity or lumpectomy cavity in a patient's breast and to facilitate delivery of a radiation balloon catheter or other treatment device into such cavities. Other body sites may also be accessed with the assembly.

Figure 1:
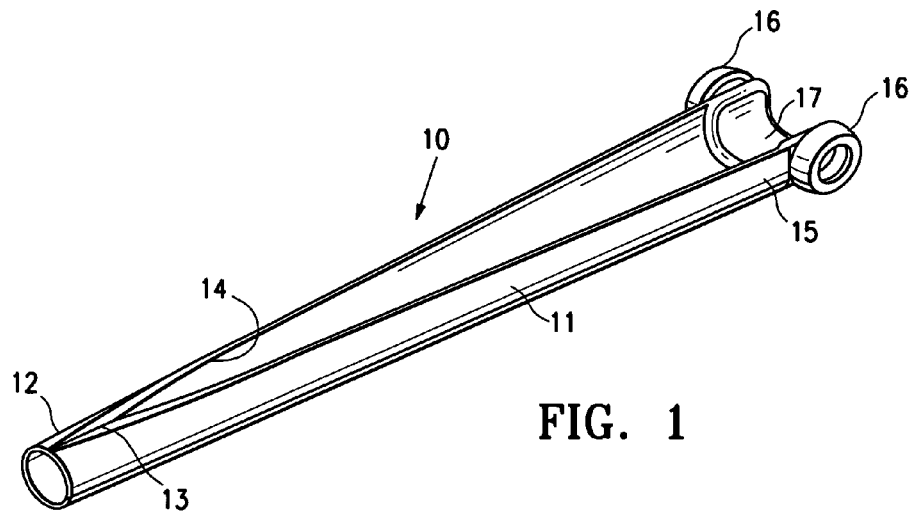
FIG. 1 is a perspective view of a split trocar sheath embodying features of the invention.

FIG. 1 illustrates an trocar sheath 10 embodying features of the invention which has an elongated shaft 11 with a cylindrically shaped distal portion 12 that has a score line 13. The shaft 11 has an elongated slit 14 that expands toward the proximal end 15 of the sheath. The proximal end 15 of the sheath 10 has finger grips 16 on opposing sides of the sheath to facilitate handling the sheath. A U-shaped support member 17 is provided on the interior of the proximal end 15 to shape the proximal end and resulting in the expanding slit and tapered interior to the sheath 10.

Figure 2:
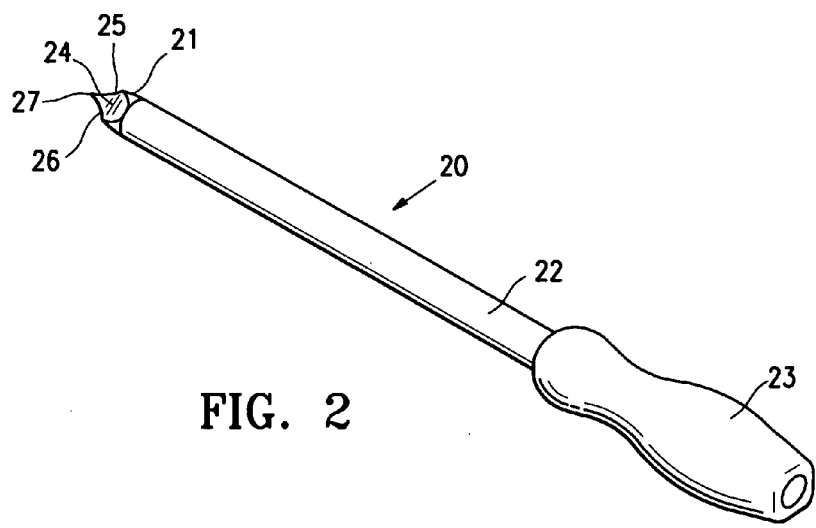
FIG. 2 is a perspective view of a trocar having a tissue penetrating distal tip, an elongated shaft and a handle on the proximal end.

A trocar 20 is shown in FIG. 2 having a tissue penetrating distal tip 21, an elongated shaft 22 and a handle 23. The tissue penetrating distal tip 21 has three concave surfaces 24, 25 and 26 extending from the sharp distal point 27 which form cutting edges. This tissue penetrating tip 21 is described in greater detail in U.S. Pub. No. 2005/0159677 which has been assigned to the present assignee and which is incorporated herein by reference. The elongated shaft 22 is configured at least at its distal portion proximal to the tip 21 to provide a friction fit with the interior of the distal portion 12 of the sheath 10.

Figure 3:
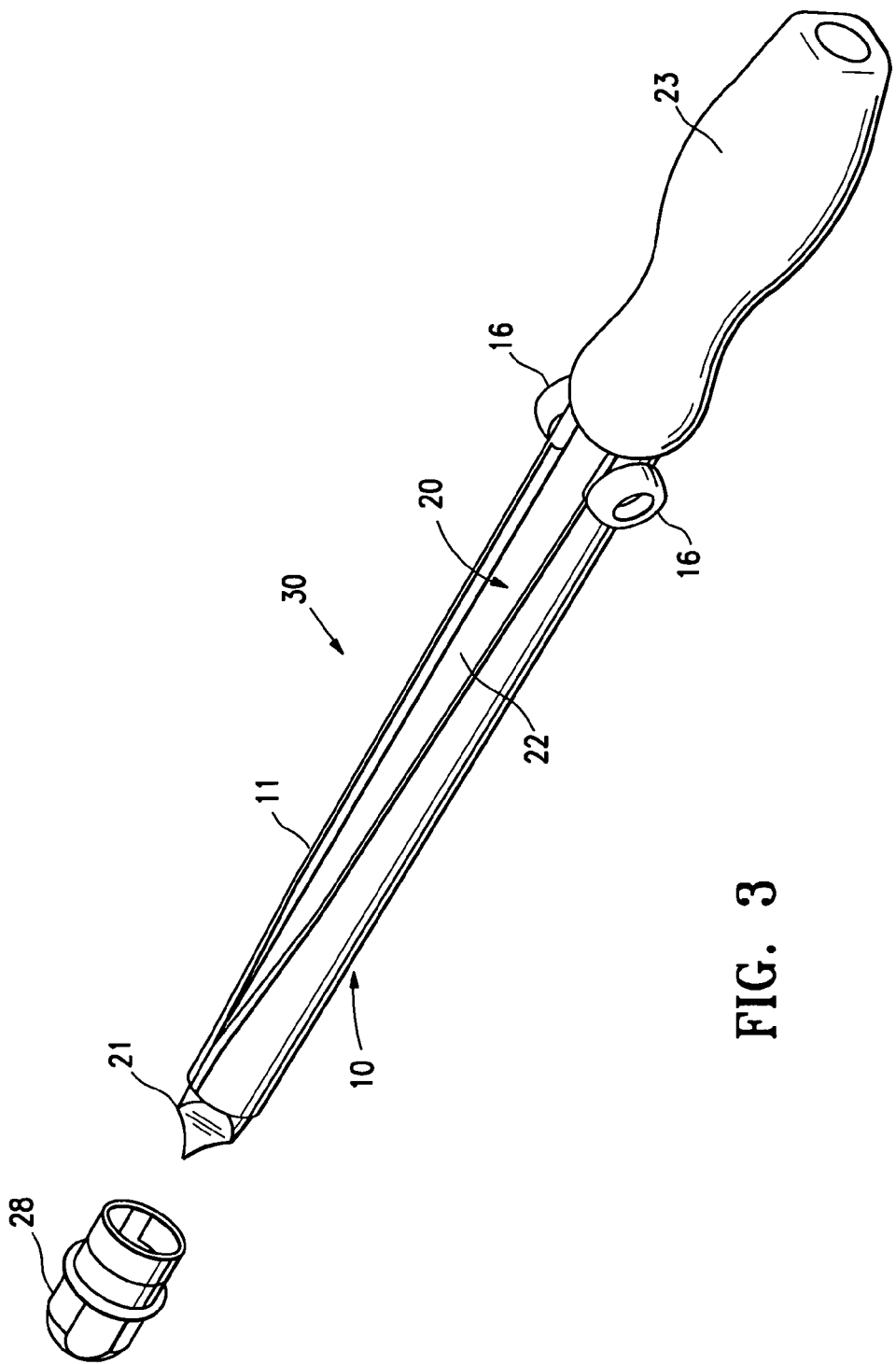
FIG. 3 is a perspective view of an assembly of the split trocar sheath shown in FIG. 1 mounted on the trocar shown in FIG. 2 with a safety cap spaced away from the distal tip of the assembly that is to be mounted over the tissue penetrating distal tip of the trocar.
Figure 4:
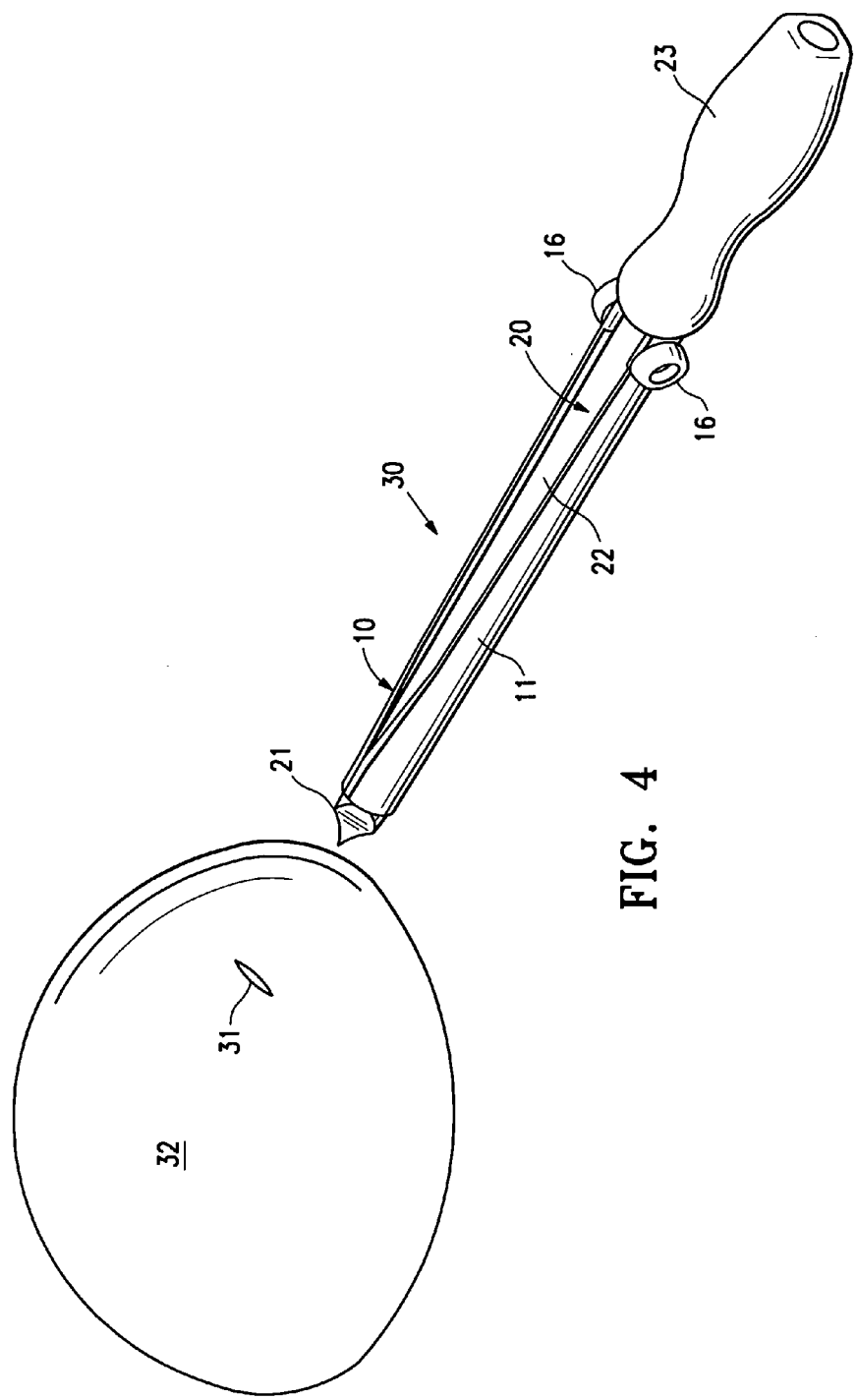
FIG. 4 is a perspective view of the assembly shown in FIG. 3 advancing toward an opening in a patient's breast.
Figure 5:
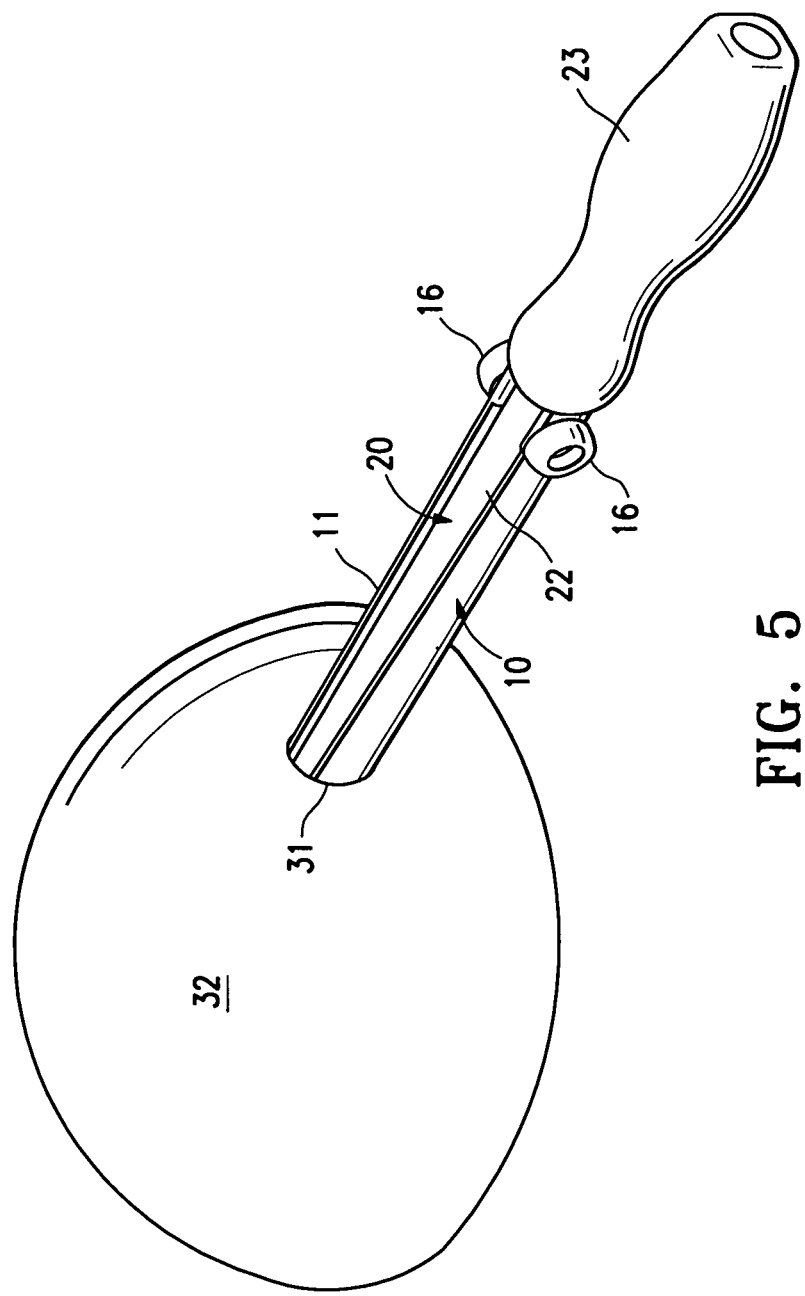
FIG. 5 is a perspective view of the assembly shown in FIG. 3 advanced within the patient's breast through the opening shown in FIG. 4.
Figure 6:
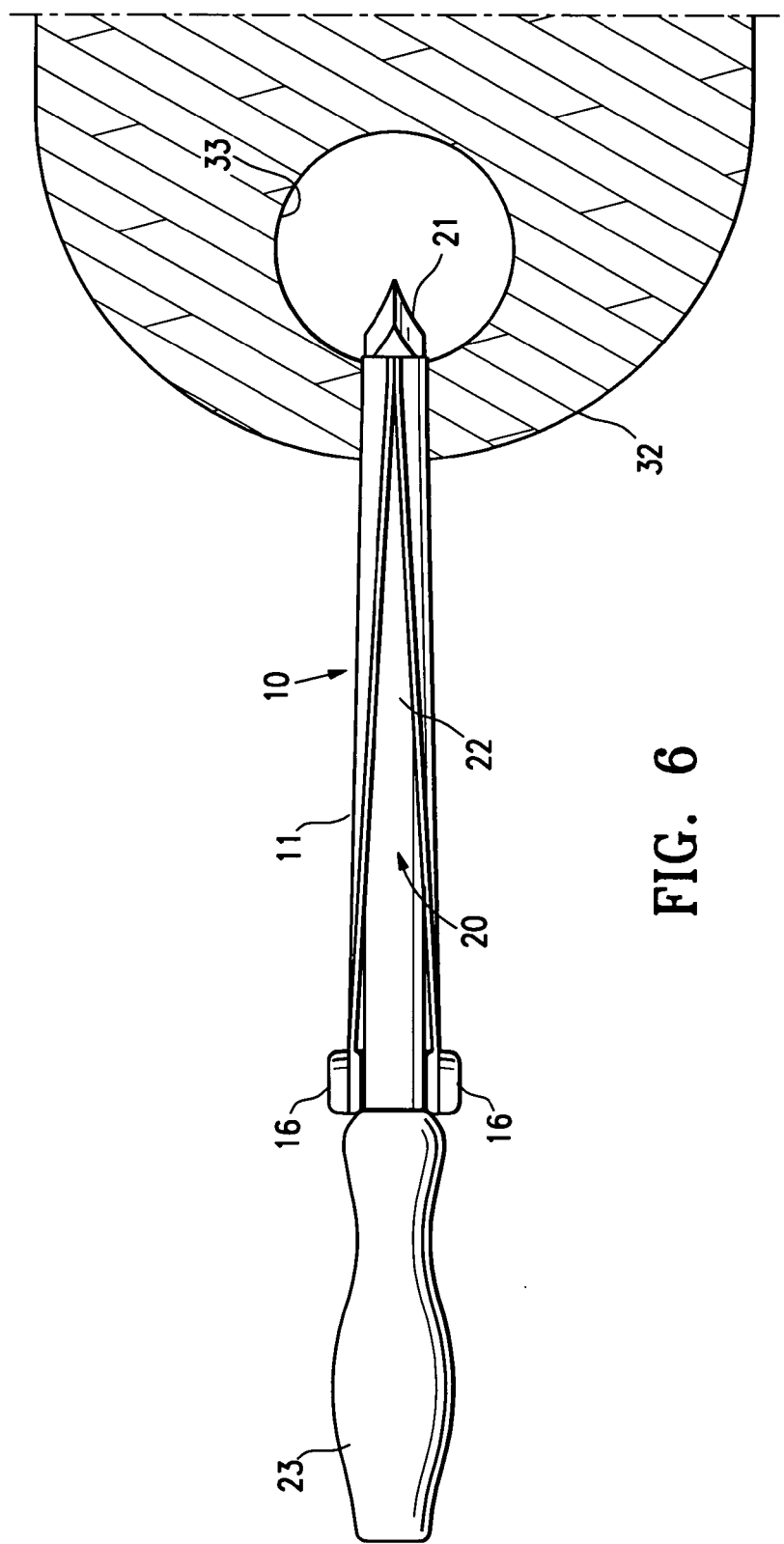
FIG. 6 is a plan view of the assembly shown in FIG. 3 advanced within the patient's breast through the opening shown in FIG. 4.
Figure 7:
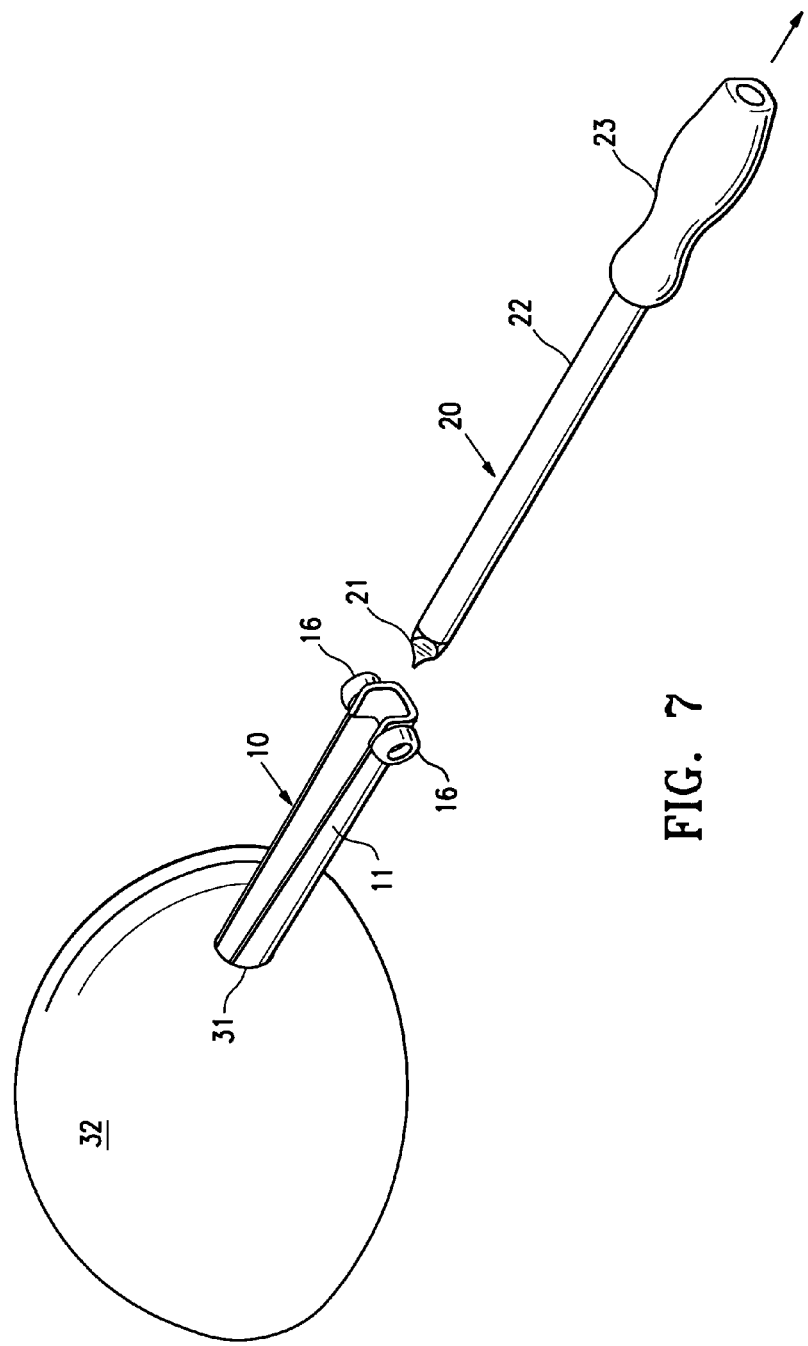
FIG. 7 is a perspective view of the withdrawal of the trocar from the trocar sheath shown in FIG. 5.

A trocar assembly 30 is shown in FIG. 3 which includes the trocar 20 disposed within the interior of trocar sheath 10 with the tissue penetrating tip extending beyond the distal end of the trocar sheath 10. A safety cap 28 is shown which is fitted over the tissue penetrating tip 21. The trocar assembly 30 is shown in FIG. 4 being advanced toward the cut 31 in a patient's breast 32 which allows access to underlying breast tissue. The tissue penetrating distal tip 21 passes through the breast tissue to the desired location within the patient's breast as shown in FIG. 5. FIG. 6 illustrates the location of the distal end of the sheath 10 with respect to cavity 33 within breast 32. Once the distal end of the trocar sheath 10 is at the desired location within the patient, the trocar 20 is withdrawn from the patient and sheath 10 as shown in FIG. 7 leaving the trocar sheath 10 at the desired location within breast 32 adjacent to cavity 33.

Figure 8:
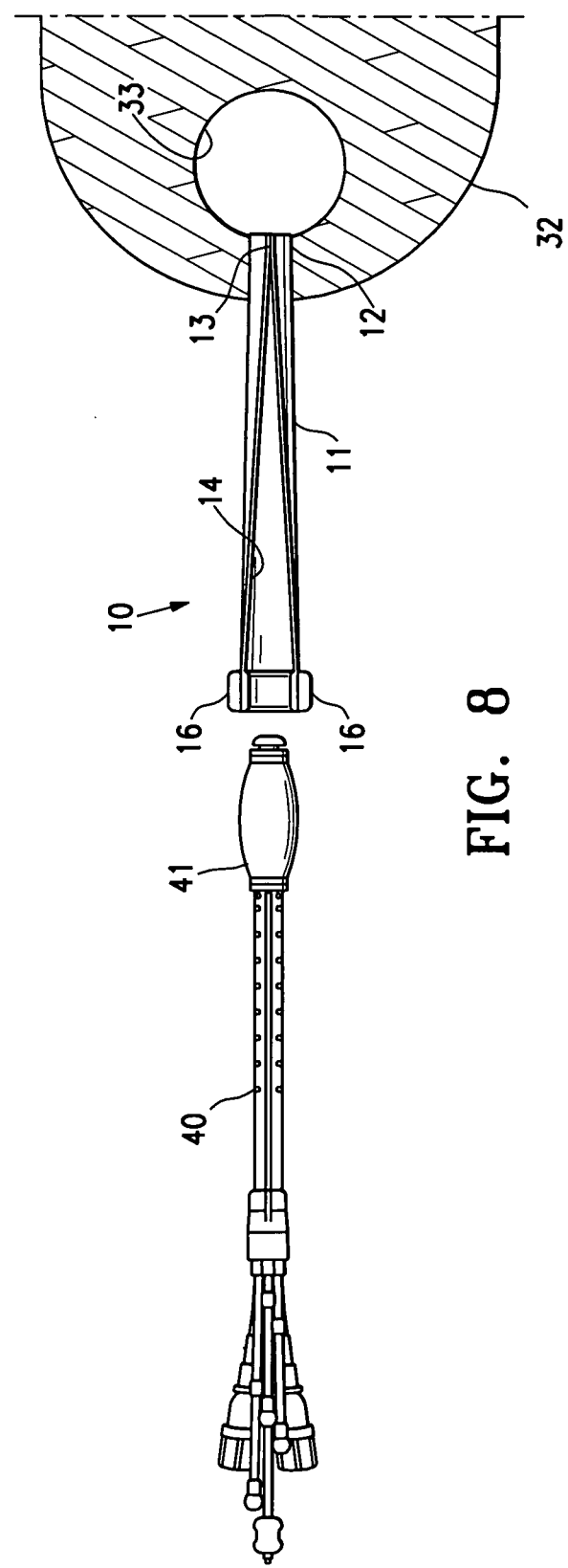
FIG. 8 is a plan view of a radiation balloon catheter being inserted into the interior of the trocar sheath positioned as shown in FIG. 7.
Figure 9:
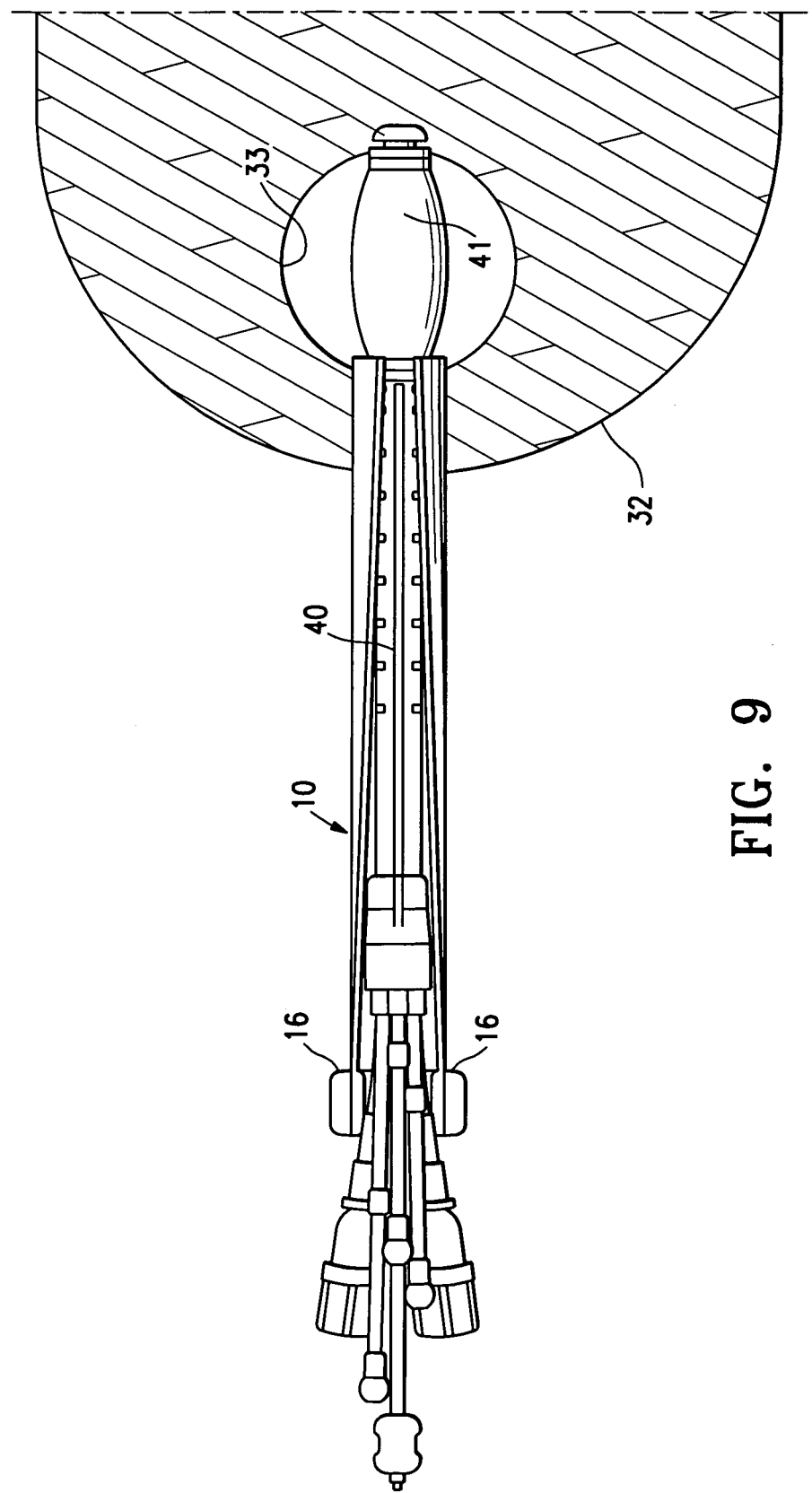
FIG. 9 is an elevational view of the radiation catheter within the trocar with the inflatable balloon portion of the catheter deployed within the patient's breast.
Figure 10:
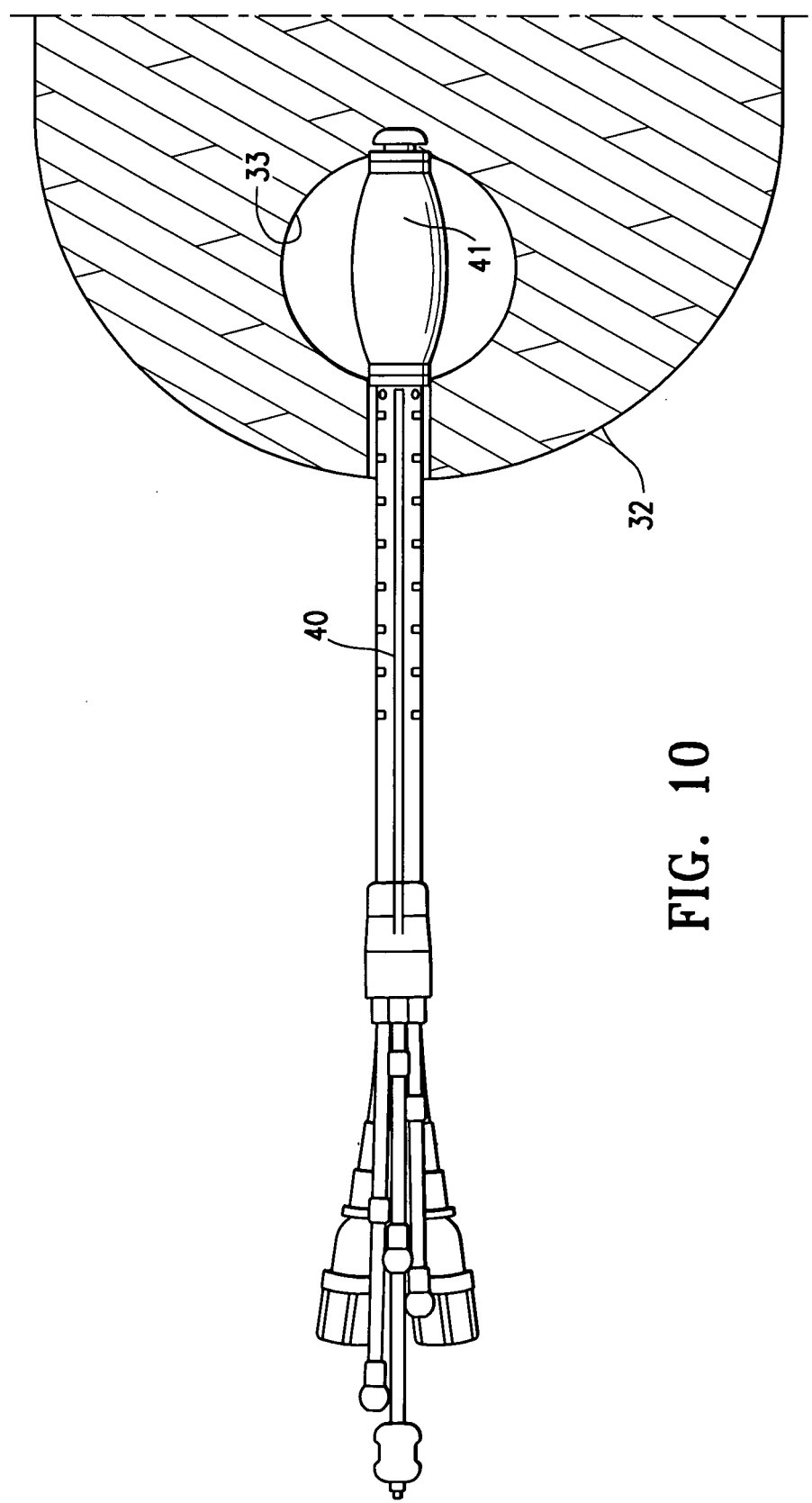
FIG. 10 is a plan view of the radiation balloon catheter with the inflatable balloon portion of the catheter deployed within the patient's breast and with the trocar sheath removed.

FIG. 8 illustrates the deployment into the trocar sheath 10 of a treatment catheter, specifically, a radiation balloon catheter 40, such as described in co-pending application Ser. No. 11/593,784, filed on Nov. 6, 2006, which has been assigned to the present assignee. The treatment catheter 40 is advanced through the interior of the trocar sheath 10, with the interior taper of the sheath guiding the distal portion of catheter 40 to the cylindrical distal portion 12 of the sheath. The transverse dimensions of the distal portion of catheter 40 are greater that the transverse dimensions of the interior of distal portion 12 of the sheath 10, so that when the distal portion of the catheter passes through the distal portion 12 of the sheath, the score line 13 is broken thereby forming a continuous slit along the length of the sheath. Once the balloon 41 on the catheter 40 is disposed within the desired intracorporeal site, the trocar sheath 10 may be withdrawn and then the balloon can be inflated by suitable inflation fluid (e.g. aqueous based contrast fluid) to secure the balloon 41 within the cavity. The trocar sheath 10 may then be withdrawn from the patient. The continuous slit allows the trocar sheath to be readily removed from the treatment catheter 40 without disturbing the position of the treatment portion of the catheter at the intracorporeal site.

A vacuum is preferably applied to the body cavity through one or more vacuum ports in the catheter 40 to conform the tissue lining the cavity to the exterior of the balloon 41. This maintains the tissue surrounding the cavity at a desired spacing from a radiation source (not shown) within the catheter balloon 41. The radiation source (not shown) may be advanced through an inner lumen of treatment catheter 40 to the treatment location within the interior of the catheter balloon 41. After the radiation treatment of the tissue lining body cavity, the radiation source may be withdrawn from the treatment catheter 40 or the catheter 40 and the radiation source may be withdrawn from the treatment site together. Multiple radiation sources may be advanced through one or more inner lumens (not shown) provided in the treatment catheter 40 so that radiation sources may be placed at several locations within the balloon 41 to develop a desired radiation pattern. The cut in the breast to expose the underlying breast tissue may be closed by suturing or a clamp after the treatment catheter 40 is removed from the patient.

Figure 11:
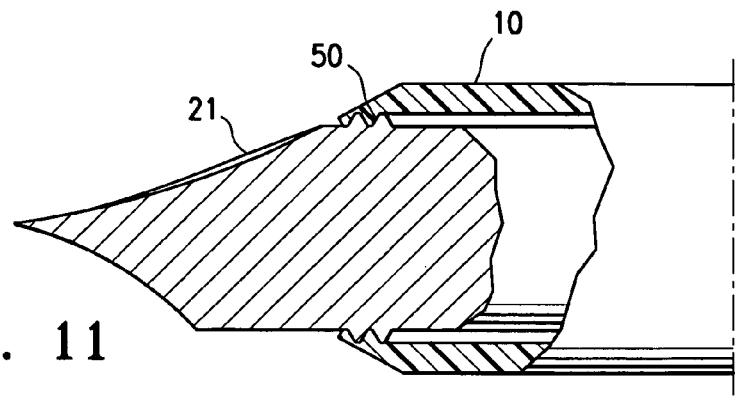
FIG. 11 is a longitudinal cross-sectional view of a releasable threaded connection between a trocar and a trocar sheath.
Figure 12:
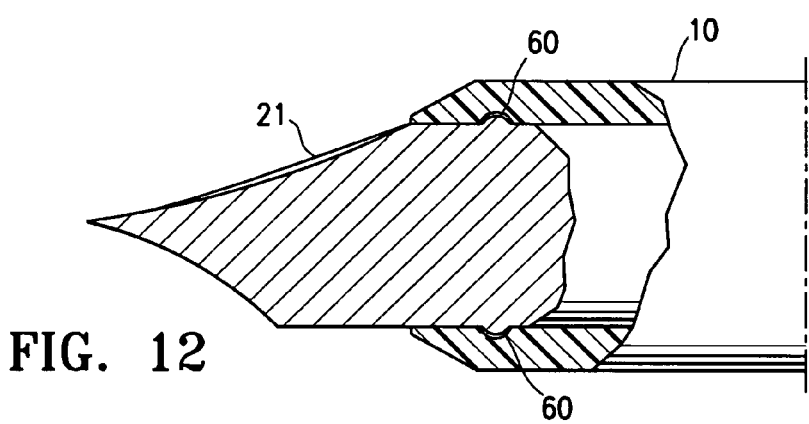
FIG. 12 is a longitudinal cross-sectional view of a releasable detent connection between a trocar and a trocar sheath.

While the aforesaid description refers to the releasable connection between the trocar shaft 22 and the cylindrical distal portion 12 of sheath 10 as a friction fit, other releasable connections may be employed. For example, a threaded connection 50 as shown in FIG. 11 or a detent connection 60 as shown in FIG. 12. Other releasable connections may be used.

The trocar sheath 10 is preferably formed of lubricious or low-friction material such as FEP or the sheath can be provided with a lubricious coating, such as a hydrophilic material. Hydrophilic coatings such as those provided by AST, Surmodics, TUA Systems, Hydromer, or STS Biopolymers are suitable.

The sheath 10 and the trocar 20 having features of the invention may also include an antimicrobial coating to minimize the risk of introducing of an infection during extended treatments. The antimicrobial coating preferably is comprised of silver ions impregnated into a hydrophilic carrier. Alternatively, silver ions may be implanted onto the surface of the device 10 by ion beam deposition. The antimicrobial coating preferably is comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable.

Figure 13:
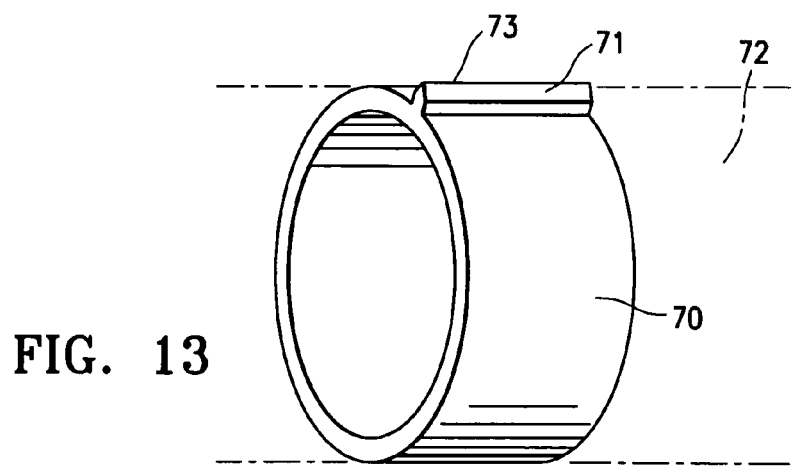
FIG. 13 is a perspective view of a collar which can be mounted onto a treatment member or other device to cut through or tear the distal cylindrical portion of the trocar sheath shown in FIG. 1.

An alternative method for breaking or tearing the distal cylindrical portion of the trocar sheath is shown in FIG. 13 which is a collar 70 with a pointed projection 71. The collar 70 can be mounted on a treatment device 72 (shown in phantom) and the edge 73 of the pointed projection can cut through or tear the distal cylindrical sheath portion (not shown in this figure).

While the invention has been illustrated and described herein primarily for treating a biopsy site or lumpectomy site within a patient's breast, it will be apparent that the invention may be employed at various locations with a patient's body. Moreover, modifications and improvements can be made to the invention. Details of the treatment devices have not been disclosed herein but can be found in applications incorporated herein by reference. To the extent not otherwise disclosed herein, materials and structure of the various components may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above are hereby incorporated by reference in their entirety.

What is claimed is:

1. A trocar assembly, comprising:
   a. a trocar having a tissue penetrating distal tip, an elongated shaft and a proximal handle portion; and
   b. a trocar sheath having a distal end, a proximal end, a distal cylindrical portion having an interior configured to provide a releasable connection with the elongated shaft of the trocar and a single slit that splits a portion of the trocar sheath, the single slit extending proximally from the distal cylindrical portion to the proximal end of the trocar, an inner portion defining at least in part a guide leading to the distal cylindrical portion, the trocar sheath having an expander collar located on an interior of a proximal end portion of the trocar sheath wherein the expander collar is a U-shaped structural support member to hold the proximal end of the sheath so as to form a longitudinally tapered interior channel, wherein the expander collar is configured to hold the single slit open at the proximal end in the absence of external forces applied to the trocar sheath.

2. The trocar assembly of claim 1 wherein the distal cylindrical portion of the sheath is a closed cylindrical portion and has a scored line aligned with the slit thereof.

3. The trocar assembly of claim 2 wherein the scored line is configured to tear upon passage therethrough of another instrument having a transverse dimension or expandable to a transverse dimension slightly larger than the transverse dimension of the closed cylindrical portion.

4. The trocar assembly of claim 1 wherein the slit expands proximally from the closed distal cylindrical portion.

5. The trocar assembly of claim 1 wherein the closed distal cylindrical portion of the sheath defines at least in part an opening in the distal end thereof.

6. The trocar assembly of claim 1 wherein the releasable connection between the trocar and the trocar sheath is a friction fit.

7. The trocar assembly of claim 1 wherein the releasable connection between the trocar and the trocar sheath is a threaded connection.

8. The trocar assembly of claim 1 wherein the releasable connection between the trocar and the trocar sheath is a detent in one of the trocar and trocar sheath and a recess or groove in the other of the trocar and trocar sheath.

9. The trocar assembly of claim 1 wherein the tissue penetrating distal tip has a sharp point and three concaved surfaces which form three cutting edges extending proximal from the sharp point.

10. A trocar sheath, comprising:
   an elongated shaft with proximal and distal ends, and having a closed cylindrical distal shaft portion;
   an elongated slit that forms a single split in the elongated shaft, the elongated slit extending proximally from the closed cylindrical distal shaft portion;
   an expander collar located at a proximal end portion of the trocar sheath wherein the expander collar is a U-shaped structural support member to hold the proximal end of the sheath so as to form a longitudinally tapered interior channel, wherein the expander collar is configured to hold the elongated slit open at the proximal end such that the single split diverges in a direction from the closed cylindrical distal shaft portion to the proximal end; and
   a score line in the closed cylindrical distal portion at least part of which is aligned with the elongated slit.

11. The trocar sheath of claim 10 wherein the expander collar causes the width of the slit to expand proximally.

12. The trocar sheath of claim 10 wherein the expander collar at the proximal end thereof has opposed exterior finger grips.

13. The trocar sheath of claim 10 wherein the U-shaped structural support member is provided with opposed exterior finger grips.

14. The trocar sheath of claim 10 wherein the distal end thereof is chamfered to provide a smooth transition with a trocar disposed in the interior channel.

15. A sheath for delivery of a catheter having a balloon on a distal portion thereof through a passageway to an intracorporeal site from which tissue has been removed, comprising:
   an elongate shaft with proximal and distal ends;
   a closed cylindrical distal shaft portion which is configured to open upon passage of the balloon on the catheter,
   an elongated expandable proximal shaft portion having free edges and having an expander collar wherein the expander collar is a U-shaped structural support member to hold the proximal end of the sheath so as to form a longitudinally tapered interior channel and configured to hold open the free edges to form a single diverging split in the elongate shaft that expands proximally from the closed cylindrical distal shaft portion, the elongated expandable proximal shaft portion having the single diverging split being configured to guide the catheter to the closed cylindrical distal shaft portion.

16. The sheath of claim 15 wherein the closed cylindrical distal shaft portion has a score line which facilitates opening of the closed cylindrical distal shaft portion upon passage of the balloon therethrough.

17. The sheath of claim 16 wherein the free edges of the proximal shaft portion define an elongated slit.

18. The sheath of claim 17 wherein the score line on the closed cylindrical distal portion is at least in part aligned with the elongated slit.

19. The sheath of claim 17 wherein the expander collar at the proximal end thereof has opposed exterior finger grips.

20. The sheath of claim 15 wherein the expander collar at the proximal end thereof has opposed exterior finger grips.

21. The sheath of claim 15 wherein the U-shaped structural support member is provided with opposed exterior finger grips.

22. The sheath of claim 14 wherein the distal end is chamfered.

23. The trocar assembly of claim 1 wherein the U-shaped structural support member is provided with opposed exterior finger grips.

24. The trocar sheath of claim 10, wherein the expander collar is located on an interior of the proximal end portion.

25. The sheath of claim 15, wherein the expander collar is located on an interior of the elongated expandable proximal shaft portion.

26. A sheath for delivery of a catheter through a passageway to an intracorporeal site, comprising:
   an elongated shaft with a proximal end and a distal end, the elongated shaft having a cylindrical distal shaft portion and an expandable proximal shaft portion,
   the expandable proximal shaft portion having a single slit defining two free edges and having an expander collar located on an interior of the expandable proximal shaft portion, wherein the expander collar is a U-shaped structural support member to hold the proximal end of the sheath so as to form a longitudinally tapered interior channel, the expander collar being configured to hold open the two free edges of the expandable proximal shaft portion in the absence of external forces applied to the sheath to form a single diverging split in the elongated shaft that expands proximally from the cylindrical distal shaft portion toward the proximal end, the expandable proximal shaft portion having the single diverging split being configured to guide the catheter to the cylindrical distal shaft portion.

27. The sheath of claim 26 wherein the cylindrical distal shaft portion has a score line aligned with the single slit which facilitates splitting of the cylindrical distal shaft portion upon passage of the catheter through the cylindrical distal shaft portion.

* * * * *